United States Patent [19]

Akers et al.

[11] Patent Number: 5,466,731
[45] Date of Patent: Nov. 14, 1995

[54] FIBRE AND FILM OF A WATER-ABSORBENT WATER-INSOLUBLE MATERIAL HAVING A MATRIX OF A COPOLYMER

[75] Inventors: Paul J. Akers, Coventry; William Brunskill, Hinckley, both of United Kingdom

[73] Assignee: Courtaulds Fibres (Holdings) Limited, London, United Kingdom

[21] Appl. No.: 338,604

[22] PCT Filed: May 18, 1993

[86] PCT No.: PCT/GB93/01012

§ 371 Date: Nov. 16, 1994

§ 102(e) Date: Nov. 16, 1994

[87] PCT Pub. No.: WO93/24684

PCT Pub. Date: Dec. 9, 1993

[30] Foreign Application Priority Data

May 22, 1992 [GB] United Kingdom ............... 9210955

[51] Int. Cl.$^6$ ........................................... C08J 5/02
[52] U.S. Cl. ................ 524/52; 524/35; 524/42; 525/55; 525/56; 525/187
[58] Field of Search ............. 524/35, 42, 52; 525/55, 56, 187

[56] References Cited

U.S. PATENT DOCUMENTS

| | | |
|---|---|---|
| 2,956,329 | 10/1960 | Touey . |
| 3,458,616 | 7/1969 | Guess et al. . |
| 4,305,901 | 12/1981 | Prince et al. . |
| 4,587,308 | 5/1986 | Makita et al. . |
| 4,861,539 | 8/1989 | Allen et al. . |
| 4,997,714 | 3/1991 | Farrar et al. . |
| 5,229,488 | 7/1993 | Nagasuna et al. . |

FOREIGN PATENT DOCUMENTS

| | | |
|---|---|---|
| 0268498 | 5/1988 | European Pat. Off. . |
| 0269393 | 6/1988 | European Pat. Off. . |
| 0342919 | 11/1989 | European Pat. Off. . |
| 0397410 | 11/1990 | European Pat. Off. . |
| 0425269 | 5/1991 | European Pat. Off. . |
| 63-210109 | 8/1988 | Japan . |
| 2082614 | 3/1982 | United Kingdom . |
| WO81/01856 | 7/1981 | WIPO . |
| WO85/02422 | 6/1985 | WIPO . |
| WO92/19799 | 11/1992 | WIPO . |

*Primary Examiner*—James J. Seidleck
*Assistant Examiner*—Terressa M. Mosley
*Attorney, Agent, or Firm*—Howson and Howson

[57] ABSTRACT

Fiber or film of water-absorbent water-insoluble fibrous material has a matrix of a crosslinked copolymer formed from 50 to 95% by weight of ethylenically unsaturated carboxylic monomer and 5 to 50% by weight of copolymerisable ethylenically unsaturated monomer. The matrix contains regions of a dispersed polymeric material, the matrix copolymer and the dispersed polymeric material being mutually immiscible and chemically substantially nonreactive under ambient conditions. The fiber or film can be produced by extruding a solution or dispersion of the polymeric material in a solution of the matrix copolymer in its non-crosslinked state into a gaseous environment.

18 Claims, No Drawings

FIBRE AND FILM OF A WATER-ABSORBENT WATER-INSOLUBLE MATERIAL HAVING A MATRIX OF A COPOLYMER

TECHNICAL FIELD

This invention relates to fibre and film of water absorbent water-insoluble material. Water-absorbent water-insoluble materials are of use in many absorbent products, particularly products for absorbing aqueous body fluids such as baby diapers, incontinence pads, sanitary napkins and tampons, and in wiping materials for mopping up spills of aqueous fluids. Most water-absorbent water-insoluble materials are available only in powder form. There are problems in retaining an absorbent powder in the desired position in the absorbent product, for example in diapers. Fibre, whether staple fibre or continuous filaments, can be more effectively retained in position by incorporation in a fabric, and fibre or film can also be effectively retained in position in other products.

BACKGROUND ART

EP-A-268498 describes a water-absorbent water-insoluble polymeric fibre, film, coating, bonding layer or foam, made by forming a substantially linear polymer of water-soluble ethylenically unsaturated monomer blends comprising carboxylic and hydroxylic monomers and then reacting the carboxylic and hydroxylic monomers in the linear polymer to form internal crosslinks within the polymer.

EP-A-269393 describes a water-absorbent water-insoluble crosslinked polymer fibre or film made by dry extrusion of a solution of a substantially linear polymer formed from a water-soluble blend of monoethylenically unsaturated monomers comprising a plasticising monomer and evaporation of the solvent. The fibre or film is further plasticised, stretched and then crosslinked.

EP-A-342919 describes film or fibre made by extrusion and stretching from a polymer of water-soluble ethylenically unsaturated monomers that include ionic monomer. A counterionic lubricant compound is absorbed into the surface of the fibre or film before or during the stretching.

EP-A-397410 describes a water-soluble linear polymer of carboxylic acid monomers such as acrylic acid and a hydroxylic monomer which can be crosslinked, after being shaped by extrusion of an aqueous solution of the polymer as fibres or film, to form crosslinks between the carboxyl and hydroxyl groups.

GB-A-2082614 describes a dry, solid, water-swellable absorbent comprising a blend of a water-insoluble absorbent polymer, which may be a covalently crosslinked or ionically complexed anionic polyelectrolyte, and an extender material selected from the group consisting of uncrosslinked derivatives, starch, montmorillonite clay, attapulgite clay, seracite, talc, kaolin, silica and mixtures thereof. It states that the blend may be used as a film, aerated film, powder or fibre, but there is no disclosure as to how a blend of water-insoluble polymer and extender can be made into a fibre.

DISCLOSURE OF INVENTION

According to the present invention fibre or film of a water-absorbent water-insoluble material has a matrix of a crosslinked copolymer formed from 50 to 95% by weight ethylenically unsaturated carboxylic monomer and 5 to 50% by weight copolymerisable ethylenically unsaturated monomer, the matrix containing regions of a dispersed polymeric material, the matrix copolymer and the dispersed polymeric material being mutually immiscible and chemically substantially non-reactive under ambient conditions.

The polymeric material of the dispersed phase may be water-soluble. The polymeric material of the dispersed phase may be self-crosslinkable and, optionally, crosslinkable with the matrix material.

The fibre or film may be formed by extruding a solution or dispersion of the polymeric material in a solution of the matrix copolymer in its non-crosslinked state into a gaseous environment wherein solvent is removed to form the fibre or film, and subsequently crosslinking the matrix copolymer and optionally the dispersed polymeric material.

The fibre or film may be stretched subsequent to formation, preferably before the crosslinking system is activated.

Although the crosslinking system can be a system that is activated by irradiation, for instance ultraviolet light, preferably it is a thermally activated system, in which event the rate of crosslinking at the temperatures prevailing during the stretching and earlier stages of the process should be such that there is substantially no crosslinking during these stages. By this means it is possible to optimise the stretching of the fibre or film while the polymer is linear and then to fix the polymer in its stretched configuration by crosslinking.

Preferably, the non-crosslinked matrix copolymer is substantially linear. It is formed from a blend of ethylenically unsaturated monomers that must be selected such that the final crosslinked copolymer is water-absorbent. Ways of selecting monomers for this purpose are known, for example from EP-A-397410 mentioned above. Generally, the blend of ethylenically unsaturated monomers is an anionic blend and usually comprises a carboxylic acid monomer, preferably with a non-ionic monomer. The monomers used in the invention may be allylic but are usually vinylic, most preferably acrylic, monomers.

Preferred carboxylic monomers are methacrylic acid or acrylic acid, but maleic acid or anhydride, iraconic acid or any of the other conventional ethylenically unsaturated carboxylic acids or anhydrides are also suitable. The copolymer can optionally additionally contain monomer units derived from an ethylenically unsaturated sulphonic acid such as 2-acrylamido-2-methyl-propane sulphonic acid or allyl sulphonic acid. Carboxylic and sulphonic monomer units may be present in the final copolymer in free acid or water-soluble salt form, suitable salts being formed with ammonia, an amine or an alkali metal. The proportion of salt and free acid groups can be adjusted after formation of the crosslinked copolymer or after polymerisation of the linear polymer or before polymerisation. Generally, the molar ratio of free carboxylic acid groups to alkali metal or other salt carboxylic acid groups in the final copolymer (and often also in the monomers that are used to form the linear copolymer) is from 1:1 to 1:10. The ratio is usually at least 1:2 and often at least 1:3. It is usually below 1:6 and often below 1:5.

When the crosslinking reaction involves reaction with the carboxylic acid groups it is usually preferred that at least some of the carboxylic acid groups should be present as free acid groups before the crosslinking occurs. For instance, for this purpose, it may be adequate for 10 to 75%, preferably 25 to 75%, of the acid groups to be in free acid form before the crosslinking occurs.

Although the linear copolymer is generally made by polymerisation of carboxylic acid monomer (in free acid or salt form), it is also possible to make the copolymer by polymerisation of monomer that can be subsequently reacted to form the carboxylic acid monomer. For instance, the carboxylic acid groups that are to be present (in free acid or salt form) in the crosslinked copolymer may be present initially in the linear copolymer in the form of hydrolysable ester groups, such as methyl ester groups, that can then be hydrolysed while in the form of a linear copolymer to yield carboxylic acid ( free acid or salt) groups.

The copolymerisable ethylenically unsaturated monomer for the matrix copolymer may be a water-soluble ethylenically unsaturated monomer such as acrylamide or may be a water-insoluble monomer, for example an olefin, such as isobutylene, an aromatic ethylenically unsaturated monomer, such as styrene or a substituted styrene, an alkyl ester of acrylic or methacrylic acid, such as methyl or ethyl acrylate or methacrylate, butyl acrylate or metacrylate or 2-ethylhexyl acrylate or methacrylate, vinyl acetate or acrylontrile. One or more copolymerisable monomers may be present. A monomer that will provide groups for internal crosslinking with the carboxylic groups (as discussed below) is usually included. Other non-ionic monomers that may be used include ethyleneically unsaturated monomers that carry a pendent group of the formula —$A_mB_nA_pR$, where B is ethyleneoxy, n is an integer of at least 2, A is propyleneoxy or butyleneoxy, m and p are each an integer less than n and preferably below 2 and most preferably zero, and R is a hydrophobic group containing at least 8 carbon atoms, as described in more detail in EP-A-213799. The comonomer(s) are generally present in amounts of at least 5% and preferably at least 10% by weight based on the monomers used for forming the copolymer, and they may be present in amounts up to about 50%, generally below 45%, by weight.

The substantially linear copolymer may be formed from the monomer blend in any conventional manner. It may be preformed and then dissolved to form a polymer solution. For instance, it may be made by reverse phase polymerisation if the monomer blend is soluble in water or by water-in-oil emulsion polymerisation if the blend is insoluble in water, e.g. at a low pH. However, this can incur the risk that the copolymer may be contaminated by surfactant and this is undesirable. Preferably, therefore, the copolymer is made by aqueous solution polymerisation or other solution polymerisation methods. It may be dried before further processing, but preferably not. Generally, it is formed by solution polymerisation in the solvent in which is it to be extruded (usually water).

The polymerisation can be conducted in conventional manner in the presence of conventional initiators and/or chain-transfer agents to give the desired molecular weight.

The concentration of copolymer in the solution to be extruded is generally in the range 5 to 50% and will be selected, having regard to the molecular weight of the copolymer, so as to give a solution having a viscosity that is convenient for extrusion. The solution can be extruded through a spinneret, suitably one of the type conventionally used in synthetic fibre production. The concentration of copolymer is usually at least 15% by weight, with values of 30% to 45%, e.g. 35% to 40%, by weight often being particularly suitable.

The solution or dispersion that is extruded may have a viscosity as low as, for instance, 20,000 mPa.s at 20° C., but generally the viscosity is at least 70,000 and usually at least 100,000 and sometimes at least 120,000 mPa.s. It can be up to 150,000 or even 200,000 mPa.s. Higher values are generally unnecessary. All these viscosities are measured at 20° C. using a Brookfield RVT spindle 7 at 20rpm. The viscosity desirably is also relatively high at the extrusion (spinning) temperature, which typically is elevated, for instance above 80° C., but below the boiling point of the copolymer solution or dispersion. Preferably, the solution or dispersion at 80° C. has a viscosity of at least 5000 or 10,000 mPa.s and most preferably at least 20,000 mPa.s. For instance, it may be in the range 50,000 to 100,000 mPa.s. These values may be obtained by extrapolation from values obtained using a Brookfield RVT viscometer spindle 7 at 20 rpm at a range of temperatures somewhat below 80° C.

The molecular weight of the linear copolymer that is extruded may be as low as, for instance, 50,000 or 100,000 but preferably is above 300,000 and most preferably is above 500,000. For instance, it may be up to 1 million or higher.

The solvent of the solution or dispersion that is extruded is usually water but can be methanol or other suitable organic solvent or may be a blend of water and organic solvent. The solvent must be volatile so as to permit rapid evaporation after extrusion. The gaseous environment into which the solution is extruded is preferably hot air. When forming fibre, the hot air can be contained in a cell of the type conventionally used for dry spinning, or flash spinning can be used. The extruded fibre can be taken up on conventional textile machinery, such as a godet, as a yarn or tow. A conventional spin finish, which is preferably non-aqueous, is usually applied to the fibre before it is taken up.

When forming film, the aqueous solution or dispersion can for example be extruded via a slit die or an annular die through a heated gaseous environment, generally hot air, on to a support surface, for example a heated rotary drum. The support surface has release properties. Drying of the film continues on the drum, and the film is stripped from the drum and taken up on rolls. The moisture content of the film as it is taken up is generally in the range 8 to 25% based on the dry weight of film, most preferably 10 to 20%.

It is preferred to stretch the fibre or film before it is collected. Stretching is effected by having the speed of the collection apparatus, for example the take-off godet, higher than the extrusion rate of the polymer solution (the linear velocity of the polymer solution through the exit capillary of the spinneret or die). The ratio of the take-off speed to the extrusion speed is generally up to 10:1 but is preferably in the range 2–8:1, most preferably 3–6:1.

The diameter of the final fibre preferably corresponds to a weight of below 20 decitex per filament, for example in the range 2 to 15 decitex per filament. This is the decitex after stretching; if stretching is used, the decitex per filament after initial extrusion may be higher than the range quoted above. If stretching is used it is carried out before crosslinking.

The linear copolymer for the matrix copolymer is crosslinked after extrusion. The crosslinking can be effected by reaction into the backbone of the linear copolymer but preferably is by crosslinking through pendent groups provided by one or more monomers that have been polymerised to form the linear copolymer. The crosslinking can be ionic, for instance as a result of exposing the linear copolymer to any of the known ionic crosslinking agents, preferably polyvalent metal compounds such as polyvalent aluminium compounds, for example aluminium sulphate. Organic compounds may be used instead of inorganic compounds to provide the crosslinking.

Preferably, however, the crosslinking is covalent between pendent groups in the linear copolymer.

The covalent crosslinking generally arises as a result of the formation of ester, amide (or imide) or urethane groups by reaction with carboxylic acid groups after extruding the copolymer. Ester groups are preferred.

The crosslinking reaction may be with an external crosslinking agent. Various systems for externally crosslinking the copolymer are described in EP-A-269393 and these can be used in the present invention. For example, the carboxyl-functional linear copolymer can be crosslinked by a diisocyanate to form urethane crosslinks or by a polyamine such as ethylene diamine to form amide crosslinks or by a polyfunctional reagent containing hydroxyl and/or epoxide groups to form ester crosslinks.

Preferably, however, the polymer is internally crosslinked by reaction between reactive groups within the extruded copolymer. Usually, the carboxylic groups act as one type of reactive group and are reactive with hydroxyl, epoxide, amino or blocked isocyanate groups. Particularly preferred systems are described in detail in EP-A-268498. In these systems the extruded copolymer is formed from a monomer blend comprising monomer that provides carboxylic acid monomer groups and monomer that provides hydroxyl groups that can react with the carboxylic acid groups to form ester crosslinks that contain only carbon and oxygen atoms in the linkages, and these carboxylic and hydroxyl groups are reacted after extrusion to form the said crosslinks. Generally, the carboxylic acid groups are provided by acrylic acid or methacrylic acid and the hydroxyl groups are provided by allyl alcohol, an epoxide-substituted vinyl monomer such as glycidyl methacrylate or a hydroxyalkyl ester of a vinyl carboxylic acid such as 2-hydroxyethyl acrylate, 2-hydroxyethyl methacrylate, 2-hydroxypropyl methacrylate or 3-hydroxypropyl methacrylate or by vinyl alcohol groups. Alternative hydroxyl group-containing monomers are those of the formula $CHR^1=CR^2-Y-M_a-OH$, where $R^1$ is hydrogen or carboxy, $R^2$ is hydrogen or methyl, Y is O, $CH_2O$ or COO, M is alkyleneoxy, for example ethylenoxy or 1,2-propyleneoxy, and a is an integer greater than 1 and preferably at least 5, as disclosed in EP-A-397410. Alternatively, the comonomer can contain a primary or secondary amine group, for example 2-aminoethyl methacrylate, which reacts to form amide crosslinks, or can contain an isocyanate group (which may need to be blocked to prevent crosslinking during extrusion), for example 2-isocyanatoethyl methacrylate, to form urethane crosslinks.

Reference should be made to EP-A-269393, EP-A-268498 and EP-A-397410 for a full disclosure of suitable materials and methods of extrusion and of crosslinking that can be used in the present invention. As stated above, heat-activated crosslinking is preferred. The temperature used to crosslink the fibre or film can for example be in the range 150° to 250° C., with the temperatures during extrusion and stretching being lower than the crosslinking temperature, preferably at least 30° C. lower.

The dispersed polymeric material can for example be: starch or chemically modified starch; one or more cellulose ethers such as carboxymethyl cellulose; polyvinyl alcohol; polyacrylamide; polyvinyl pyrrolidone; a polyalkylene oxide; or a polymer of an unsaturated sulphonic ester. The material can alternatively be a polymer of an unsaturated carboxylic ester, provided that the composition is sufficiently different from the matrix copolymer to ensure immiscibility. Under the conditions used to crosslink the matrix copolymer the dispersed polymer may or may not also crosslink, depending upon its chemical nature. It may be preferable for the dispersed polymer to be crosslinkable, in which case it may be preferred to incorporate a latent crosslinking agent during its preparation, for example a heat-activated crosslinking agent if the matrix copolymer is to be crosslinked by heat.

The dispersed polymeric material is preferably water-soluble. A solution of the dispersed polymeric material in water can be prepared by direct polymerisation of one or more water-soluble monomers in water, by direct dissolution of solid polymer in water, or by preparation of a latex by inverse emulsion polymerisation followed by evaporation of the nonaqueous solvent, or by chemical reaction on a slurry or latex of a water-insoluble precursor polymer. An example of such a reaction is hydrolysis of a latex of polyvinyl acetate to prepare an aqueous solution of polyvinyl alcohol.

Prior to extrusion, it is necessary to produce a dispersion of a solution of the dispersed polymeric material in a solution of the matrix copolymer. The dispersion is usually produced by mixing an aqueous solution or emulsion of the polymeric material with an aqueous solution of the matrix copolymer. The size of the dispersed polymer solution phase should preferably be small to ensure good extrusion continuity. Mixing can be carried out mechanically, for example using a high-shear mixer, ultrasonically or by pumping the solutions through a static mixer. It is preferable that the dispersion is extruded into fibre or film as soon as possible after mixing of the solutions, as the dispersed phase will increase in size with time. Dispersion agents such as block or graft copolymers can optionally be incorporated to improve the stability of the dispersion.

The dispersed polymeric material may reduce the viscosity of the copolymer solution or may be chosen to improve the properties of the fibre or film; for example when it is polyvinyl alcohol it may modify the absorption and retention characteristics of the fibre or film or increase the flexibility of the fibre or film. A natural polymer such as starch or a chemically modified starch can be used as the dispersed polymeric material to enhance the biodegradability of the fibre or film.

According to one aspect of the invention the dispersed polymeric material improves the absorbency and retention characteristics of the fibre or film for liquids. The absorbency can be measured by the free swell test, in which 0.5 g fibre is dispersed in 30 ml aqueous liquid and left for 5 minutes. The aqueous liquid used is generally 0.9% by weight saline solution, which is generally absorbed to a similar extent to bodily fluids such as urine. The test can alternatively be carried out with either tap water or demineralised water, but results quoted below are for 0.9% saline solution. For all absorbency measurements, the fibre is conditioned at 65% relative humidity and 20° C. before being tested. The dispersion is then filtered through a sintered Mark 1 funnel of pore size 100–160 microns and is left for 5 minutes, or until it stops dripping. The water filtered through the funnel is weighed and the weight of water absorbed by the fibres is calculated by subtraction.

In an addition to the above test, the retention by the fibre or film of the aqueous liquid such as saline solution after application of pressure is measured by weighing the water expressed after application of pressure at about 3.4 KPa for 5 minutes or until dripping stops.

In a further test of absorption, the absorbency under load is measured by maintaining the fibre or film in contact with a 0.9% by weight saline solution for an hour while applying a load of 1.7 KPa.

The presence of dispersed polymeric material in the fibre or film may improve the absorbency, retention or absorbency under load, as measured by these tests, or the dryness to touch of the gel formed after the fibre or film has absorbed aqueous fluid. The dispersed polymeric material may also make these properties of the fibre or film less dependent upon the concentration of ionic salts in the aqueous fluid.

The proportion of dispersed polymeric material in the fibre or film is generally up to 20% by weight, for example up to 15%, preferably up to 10%, by weight, based on the copolymer. Usually, the proportion of dispersed polymeric material is at least 1% by weight to achieve a significant effect. For many purposes the proportion of dispersed polymeric material is up to 5% by weight, and preferably at least 2%. The particle size of the dispersed polymeric material in the fibre or film can for example be up to about 20 or 25 microns, more usually up to 15 microns. Whilst in general the size of the particles can be up to about half the diameter of the fibre or thickness of the film, a relatively low particle size, for example less than 10 microns and preferably less than 5 microns, is preferred when the proportion of dispersed polymeric material in the fibre or film is above 5% by weight. A particle size of less than 1 micron may be preferred.

The polymer solution containing dispersed polymeric material is capable of being converted into fibre (including filaments and fibrils) or film (including sheet and coatings) with evaporation of the solvent after shaping. Fibre produced can be further processed into milled fibres, chopped fibres, yarns, webs or woven, knitted or nonwoven fabrics.

The water-absorbent water-insoluble fibre or film of the present invention can be used in various products. It can, for example, be used in absorbent personal products such as tampons, disposable diapers, sanitary napkins or incontinence pads. The absorbent fibre is preferably used in combination with other fibres, for example cellulosic fibres such as cotton or regenerated cellulose fibres, including multi-limbed cellulose fibres as described in EP-A-301874, or polypropylene or polyester fibres. The absorbent fibre can be intimately mixed with said other fibres, for example by carding or air-laying the fibres together to form a web of mixed fibres. Alternatively, the absorbent fibre or film can be used as a layer, for example a non-woven fabric of absorbent fibre, sandwiched between layers of other fibres. The proportion of absorbent fibre in a blend with cellulosic fibres for absorbent products can for example be at least 5% and up to 95%, preferably at least 10% and up to 50%, by weight. The absorbent fibre can also be used at similar levels in conjunction with fluffed wood pulp or synthetic fibre pulp, for example polyolefin pulp, in absorbent products.

A yarn, woven fabric or nonwoven fabric comprising the absorbent fibre can be used as a swellable material which prevents ingress of water in underground cables. A yarn or fabric tape or an absorbent film can be used to wrap cable or can be laid longitudinally in the cable.

The absorbent fibre or film can be used in many other applications of the types described in Research Disclosure, January 1992 at pages 60–61, for example in filters, absorbent liners or mats for packaging, disposable wipes, mats, shoe insoles or bed sheets, swellable gaskets or seals, moisture-retention mats in horticulture, moisture-retaining packaging or swellable self-sealing stitching threads.

The invention is illustrated by the following Examples:

Example 1

A 40% by weight solution of "Goshenol GL05" (Trade Mark) poly(vinyl alcohol) was prepared at 70° C. This solution was added to a 38% by weight aqueous solution of a copolymer of 78 mole % acrylic acid (75% neutralised as sodium salt), 20 mole % methyl acrylate and 2 mole % hexapropylene glycol monomethacrylate. The suspension was added at 55° to 65° C. and stirred with a paddle stirrer. After 2 hours an even dispersion was obtained, containing approximately 38% by weight solids and 2% by weight polyvinyl alcohol based on total polymer.

This dispersion was spun into filaments through a spinneret into a cell where water was evaporated from the filaments. The temperature of the dispersion at the spinneret was between 90° and 100° C. The cell was heated by tube wall heaters at 150° C. The filaments were taken up at approximately 200 m/min to give a fibre of approximately 15 dtex. Samples of the resulting multifilament tow were crosslinked by heating in air under the conditions shown in Table 1. The free swell absorbency, retention and absorbency under load (AUL) of the resulting fibres were measured in each case by the methods described above.

TABLE 1

| Crosslink time at 210° C. | Free Swell g/g | Retention g/g | AUL g/g |
| --- | --- | --- | --- |
| 6 mins | 49.2 | 32.2 | 26.8 |
| 8 mins | 46.2 | 31.7 | 24.2 |
| 10 mins | 39.3 | 24.9 | 21.5 |
| 12 mins | 39.8 | 25.2 | 23.8 |

The results indicate that the fibres have a relatively high absorbency under load. At all degrees of crosslinking the absorbency under load of the fibres tested was higher than that of similar fibres containing no polyvinyl alcohol which had an equally high free swell absorbency. The fibres appeared more flexible than similar fibres containing no polyvinyl alcohol.

Example 2

Starch was dissolved in water and mixed with a solution in water of a copolymer of acrylic acid, methyl acrylate and hexapropylene glycol monomethylacrylate in the ratio 60:35:5 by weight to produce a 38% by weight dispersion containing 5% by weight starch based on total polymer. The conditions of mixing were as described in Example 1. The dispersion produced was dry spun as described in Example 1. The spun filaments were crosslinked at 200° C. for 10 minutes to produce superabsorbent filaments. The water absorbency and retention of the filaments were similar to those of similar filaments without the starch, and the filaments of Example 2 had enhanced biodegradability.

We claim:

1. Fibre or film of a water-absorbent water-insoluble material having a matrix of a crosslinked copolymer formed from 50 to 95 % by weight of ethylenically unsaturated carboxylic monomer and 5 to 50% by weight of copolymerisable ethylenically unsaturated monomer, the matrix containing regions of a dispersed polymeric material, the matrix copolymer and the dispersed polymeric material being mutually immiscible and chemically substantially non-reactive under ambient conditions.

2. Fibre or film according to claim 1, wherein the dispersed polymeric material is a water-soluble polymer.

3. Fibre or film according to claim 1, wherein the dispersed polymeric material is crosslinked.

4. Fibre or film according to claim 1, wherein the dispersed polymeric material is starch or a chemically modified starch and the fibre or film has enhanced biodegradability compared to fibre or film formed of the matrix copolymer alone.

5. Fibre or film according to claim 1 wherein the dispersed polymeric material is polyvinyl alcohol and the fibre or film has increased absorbency under load and/or increased flexibility compared to fibre or film formed of the matrix copolymer alone.

6. Fibre or film according to claim 1 wherein the dispersed polymeric material is a cellulose ether, a polyalkylene oxide or a polymer of an unsaturated sulphonic ester.

7. Fibre or film according to claim 1 wherein the dispersed polymeric material is present at 1 to 10% of the dry weight of the fibre or film.

8. Fibre or film according to claim 7, wherein the dispersed polymeric material is present at up to 5% of the dry weight of the fibre or film.

9. Fibre or film according to claim 1 wherein the matrix copolymer is crosslinked by ester crosslinks.

10. Fibre or film according to claim 9, wherein the copolymerisable ethylenically unsaturated monomer of the matrix copolymer consists at least partly of a hydroxyl-functional or epoxide-functional comonomer, and that the ester crosslinks are formed by reaction between carboxylic acid groups derived from the carboxylic monomer and hydroxyl or epoxide groups derived from the copolymerisable monomer.

11. A process for the production of fibre or film of a water-absorbent water-insoluble material having a matrix of a crosslinked copolymer formed from 50 to 95% by weight of ethylenically unsaturated carboxylic monomer and 5 to 50% by weight of copolymerisable ethylenically unsaturated monomer, the. matrix containing regions of a dispersed polymeric material, the matrix copolymer and the dispersed polymeric material being mutually immiscible and chemically substantialially non-reactive under ambient conditions, wherein a solution or dispersion of the polymeric material in a solution of the matrix copolymer in its non-crosslinked state is extruded into a gaseous environment wherein solvent is removed to form the fibre or film, and the matrix copolymer, and optionally the dispersed polymeric material, is subsequently crosslinked.

12. A process according to claim 11, wherein the solution of the matrix copolymer is an aqueous solution.

13. A process according to claim 12, wherein the concentration of the matrix copolymer in the aqueous solution is 30 to 45% by weight.

14. A process according to claim 11, wherein the solution or dispersion is extruded at a temperature which is above 80° C. but below the boiling point of the copolymer solution or dispersion.

15. A process according to claim 11, wherein the solution or dispersion has a viscosity at 80° C. of at least 20,000 mPa.s.

16. A process according to claim 11, wherein the solution or dispersion is extruded through a spinneret to form fibres.

17. A process according to claim 11, wherein the crosslinking is effected by heating the fibre or film at a temperature in the range 150° to 250° C.

18. A process according to claim 11, wherein the fibre or film is stretched before effecting the crosslinking of the copolymer.

* * * * *

UNITED STATES PATENT AND TRADEMARK OFFICE
CERTIFICATE OF CORRECTION

PATENT NO. : 5,466,731
DATED      : November 14, 1995
INVENTOR(S) : Paul J. Akers and William Brunskill It is certified that error appears in the above-indentified patent and that said Letters Patent is hereby corrected as shown below:

Col. 2, line 39, delete the word "iraconic" and substitute therefore -- itaconic --.

Signed and Sealed this

Fourth Day of June, 1996

Attest:

BRUCE LEHMAN

Attesting Officer    Commissioner of Patents and Trademarks